United States Patent
Aneas

(10) Patent No.: US 11,383,046 B2
(45) Date of Patent: Jul. 12, 2022

(54) AFTER-USE SAFETY SYSTEM FOR A SYRINGE WITH BONDED NEEDLE AND SYRINGE EQUIPPED WITH SUCH A SYSTEM

(71) Applicant: BIOCORP PRODUCTION, Issoire (FR)

(72) Inventor: Daniel Aneas, Menetrol (FR)

(73) Assignee: BIOCORP PRODUCTION, Issoire (FR)

(*) Notice: Subject to any disclaimer, the term of this patent is extended or adjusted under 35 U.S.C. 154(b) by 165 days.

(21) Appl. No.: 16/768,890

(22) PCT Filed: Dec. 5, 2018

(86) PCT No.: PCT/EP2018/083605
§ 371 (c)(1),
(2) Date: Jun. 2, 2020

(87) PCT Pub. No.: WO2019/110644
PCT Pub. Date: Jun. 13, 2019

(65) Prior Publication Data
US 2021/0162138 A1 Jun. 3, 2021

(30) Foreign Application Priority Data
Dec. 6, 2017 (FR) .................................... 1761719

(51) Int. Cl.
*A61M 5/32* (2006.01)
(52) U.S. Cl.
CPC .......... *A61M 5/326* (2013.01); *A61M 5/3272* (2013.01)

(58) Field of Classification Search
CPC .. A61M 5/326; A61M 5/3272; A61M 5/3271; A61M 2205/273; A61M 5/321
See application file for complete search history.

(56) References Cited

U.S. PATENT DOCUMENTS

2005/0267416 A1 12/2005 Mohammed
2008/0167611 A1 7/2008 Miller
(Continued)

FOREIGN PATENT DOCUMENTS

EP 3106191 A1 12/2016
WO 2013134465 A1 9/2013
(Continued)

OTHER PUBLICATIONS

INPI Rapport de Recherche Preliminaire for Patent Application No. FR 1761719, Aug. 9, 2018, 2 pp.
(Continued)

*Primary Examiner* — Nathan R Price
*Assistant Examiner* — Melissa A Snyder
(74) *Attorney, Agent, or Firm* — Soquel Group LLC

(57) ABSTRACT

An after-use safety system for a syringe, including a barrel which defines a central axis along which it can move in translation and which includes a radial opening forming a guidance path for a pin, an immobiliser, which is arranged inside the barrel and which includes the pin interacting with the barrel, and a return spring configured to elastically load the barrel forwards with respect to the immobiliser, the immobiliser including a radial stopping means for immobilising the barrel along one axis radial to the central axis when the barrel is forced towards the rear after use of the syringe.

10 Claims, 7 Drawing Sheets

(56) References Cited

U.S. PATENT DOCUMENTS

2009/0005742 A1* 1/2009 Liversidge ............ A61M 5/326
                                                    604/263
2011/0118667 A1* 5/2011 Zaiken .................. A61M 5/326
                                                    604/138

FOREIGN PATENT DOCUMENTS

WO    2016120185 A2    8/2016
WO    2016207196 A1    12/2016

OTHER PUBLICATIONS

International Search Report for Patent Application No. PCT/EP2018/083605, dated Feb. 22, 2019, 3 pp.

* cited by examiner

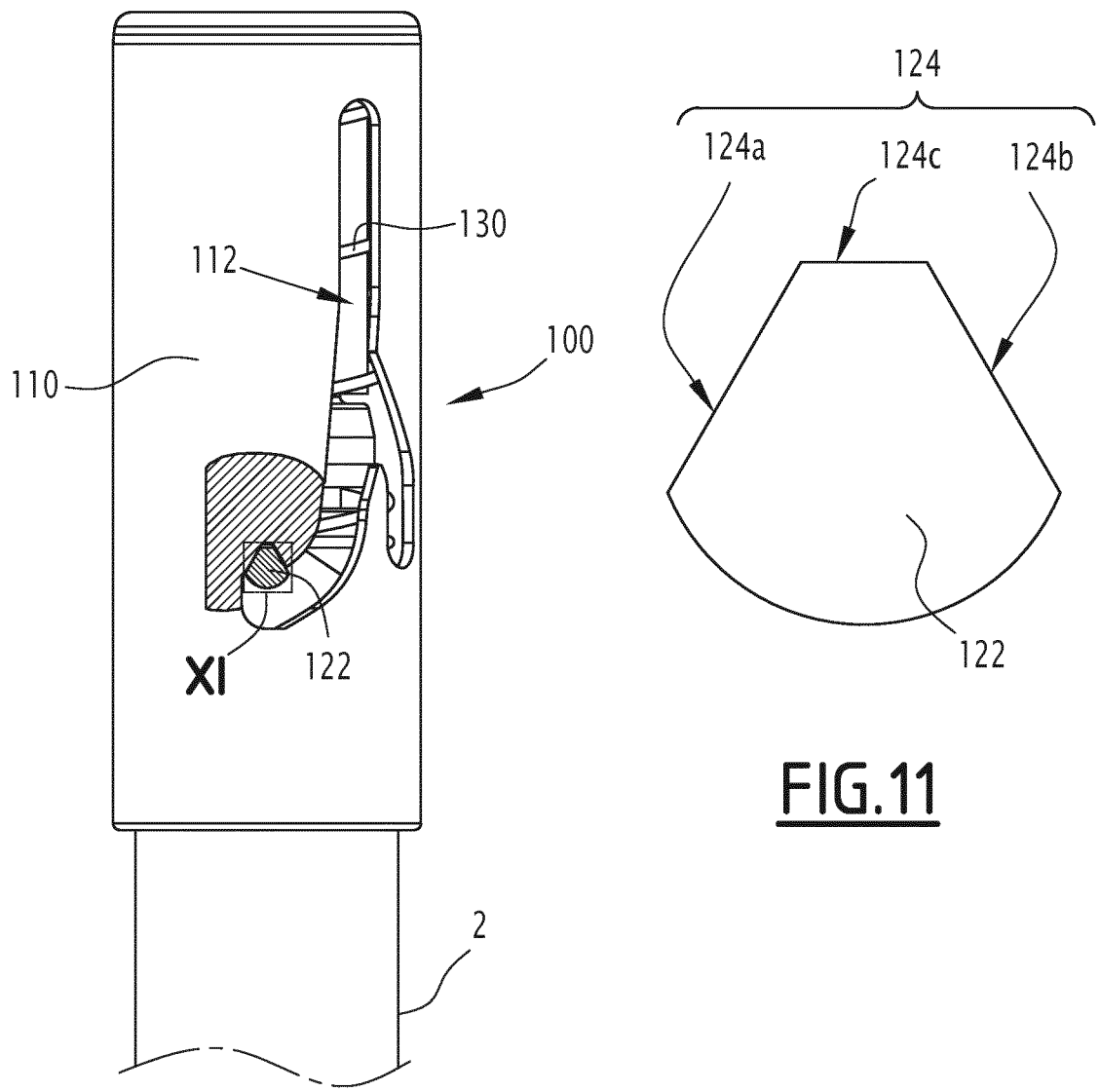

AFTER-USE SAFETY SYSTEM FOR A SYRINGE WITH BONDED NEEDLE AND SYRINGE EQUIPPED WITH SUCH A SYSTEM

CROSS-REFERENCE TO RELATED APPLICATIONS

This application claims benefit under 35 USC § 371 of PCT Application No. PCT/EP2018/083605 entitled AFTER-USE SAFETY SYSTEM WITH BONDED NEEDLE AND SYRINGE EQUIPPED WITH SUCH A SYSTEM, filed on Dec. 5, 2018 by inventor Daniel Aneas. PCT Application No. PCT/EP2018/083605 claims priority of French Patent Application No. 17 61719, filed on Dec. 6, 2017.

FIELD OF THE INVENTION

The present invention relates to an after-use safety system for a syringe with bonded needle.

BACKGROUND OF THE INVENTION

In the medical field, an after-use safety system is a system making it possible to protect (or cover) the needle of a syringe at the end of an injection. This makes it possible to avoid injury with the needle when the latter is removed from the patient's body and to combat the transmission of diseases, such as HIV.

Typically, FIGS. 1 to 5, taken from publication WO 2016/120185 A1, show an exemplary after-use safety system. This system comprises a barrel 18 that defines a central axis X1 along which it is translatable and which comprises two radial openings 180 each forming a guide path for a pin 160. The two pins 160 belong to an immobilizer 16b, which is arranged inside the barrel. The system also comprises a return spring 20, configured to charge the barrel 18 resiliently in the forward direction relative to the immobilizer 16b. Each guide path 180 is globally in the shape of an asymmetrical Y, with the branches of the Y extending toward the rear. The branches of the Y are referenced 180a and 180c, while its central portion is referenced 180b. This central portion 180b is a straight portion, i.e., a corridor.

Advantageously, each guide path 180 also comprises, at one end, a bent segment forming a housing 180d, inside which the corresponding pin 160 is received when the barrel 18 is forced toward the rear, so as to block the movement of the barrel toward the rear after use of the syringe. Reference is made to locking means in the forward position.

When the syringe is placed against the epidermis of a patient, the pressure exerted by the barrel on the skin causes the barrel 18 to withdraw. The spring 20 is then compressed and the needle 10 penetrates the epidermis. The pins 160 move from the branch 180a into the central portion 180b. When the needle is completely pushed into the epidermis, the user presses on the rod 4 of the syringe to inject the active ingredient contained inside the syringe 1 into the body of the patient.

When the user removes the syringe from the patient's body, the barrel 18 is elastically returned to the forward position by the spring 20. The barrel then returns to cover the needle and the pins slide in the corridor 180b of the openings toward the branch 180c. The syringe is then in the configuration of FIG. 4, which is in an end-of-injection configuration.

If, after use of the syringe, a clumsy user presses on the barrel, that is to say, tries to move the barrel toward the rear, the pins 160 then move, as visible in FIG. 5, into the housing 180d and the movement of the barrel toward the rear is blocked. This constitutes an additional safety, since the needle can no longer be exposed at the end of the injection.

Nevertheless, the barrel is generally made from plastic, with a relatively small wall thickness, such that the barrel has a certain propensity for deforming when it is forced in the backward direction, that is to say, when an axial force is applied to a longitudinal end of the barrel. This deformation is then also favored by the presence of guide paths formed in the barrel, which decrease the mechanical strength of the barrel.

Thus, one can see in practice that when the axial force reaches approximately 20N, the barrel tends to bend and ovalize. The pins then enter inside the barrel and leave their guide path: the system is unlocked.

SUMMARY OF THE DESCRIPTION

The invention more particularly aims to address these drawbacks by proposing a new after-use safety system, which better withstands a forced unlocking attempt.

One obvious solution to improve the resistance of the assembly to a forced unlocking attempt consists of increasing the size of the pins and/or the barrel. Conversely, the system would not be as radially compact, which would pose problems during the manufacture of the syringes. Typically, the system would no longer be compact enough to be able to penetrate the housings of the standard supports used in the field (on this subject, see the issue set out in publication WO 2016/120185 A1, the content of which is incorporated herein by reference).

To that end, the system relates to an after-use safety system for a syringe, this system comprising a barrel, which defines a central axis along which it can move in translation and which comprises a radial opening forming a guidance path for a pin, an immobilizer, which is arranged inside the barrel and which comprises the pin interacting with the barrel, and a return spring configured to elastically load the barrel forwards with respect to the immobilizer. According to the invention, the immobilizer comprises a radial stopping means for immobilizing the barrel along one axis radial to the central axis when the barrel is forced towards the rear after use of the syringe.

According to advantageous, but optional aspects of the invention, the system may comprise one or more of the following features, considered in any technically allowable combination:

- the radial stopping means is part of the pin.
- the radial stopping means is a radial end part of the pin, which is arranged opposite the base of the pin.
- the pin comprises a recess at least partially covered by the radial stopping means and in that this recess is dimensioned to receive a portion of the barrel when the barrel is forced toward the rear after use of the syringe.
- the walls of the recess comprise two oblique faces that converge one toward the other, preferably symmetrically, in the forward direction.
- said part of the barrel comprises two oblique faces complementary to those of the pin, the oblique faces of said part of the barrel cooperating with the oblique faces of the pin when the barrel is forced toward the rear after the use of the syringe.
- the radial stopping means comprises a stopping surface interacting with a complementary surface of the barrel when the barrel is forced toward the rear after use of the syringe.

the stopping surface is non-perpendicular to the central axis, preferably inclined relative to the central axis.

the stopping surface comprises a normal oriented toward the inside of the system.

The invention also relates to a syringe equipped with an after-use safety system as previously defined.

BRIEF DESCRIPTION OF THE DRAWINGS

The invention and other advantages thereof will appear more clearly in light of the following description of one embodiment of an after-use safety system according to its principle, provided solely as an example and done in reference to the drawings, in which:

FIG. 10 is a cross-section of the after-use safety system, then mounted on a syringe, the section plane passing, in this view, through the base of a pin of the immobilizer;

FIG. 11 is an enlarged view of box XI of FIG. 10;

DETAILED DESCRIPTION

Figure 1:
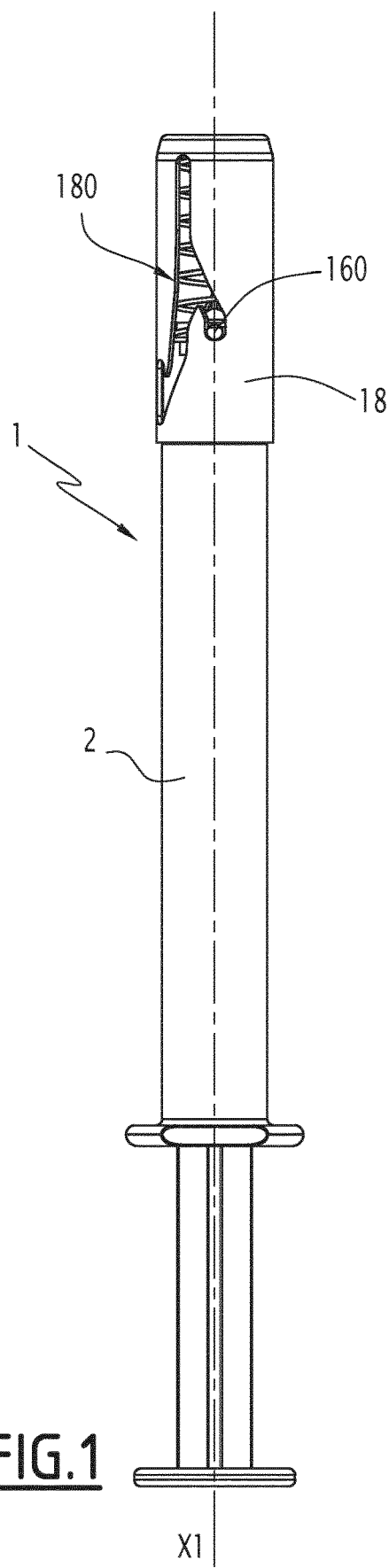
FIGS. 1 to 5 are views of a syringe equipped with an after-use safety system of the prior art, and in particular show the different configurations of the system when it is mounted on a syringe and the syringe is used to inject an active ingredient inside the body of a patient.
Figure 2:
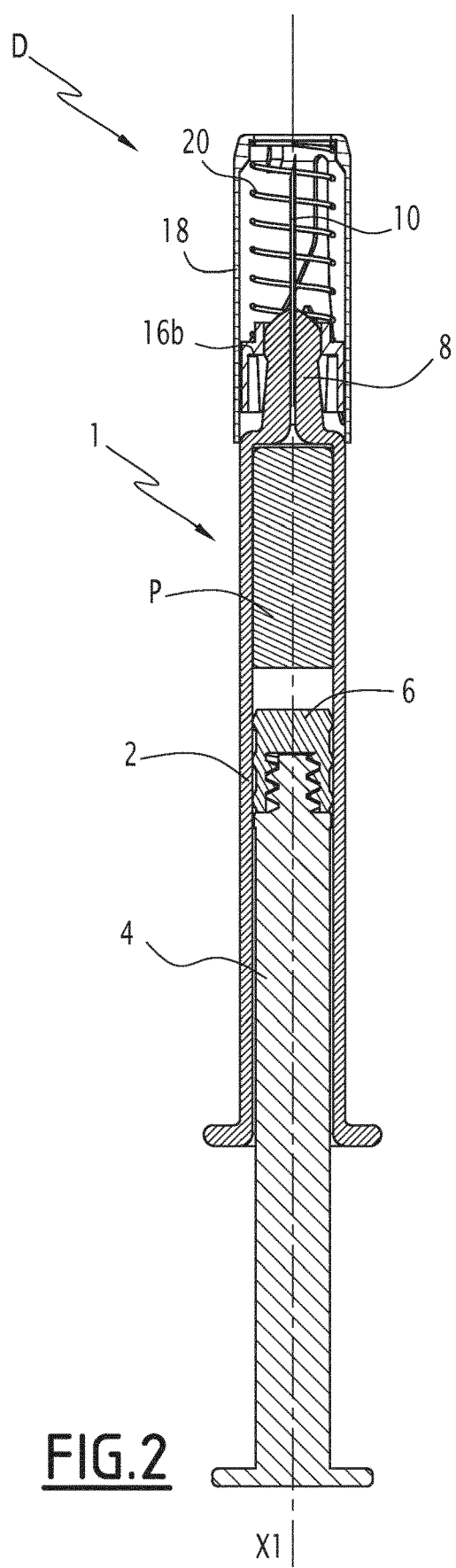
Figure 3:
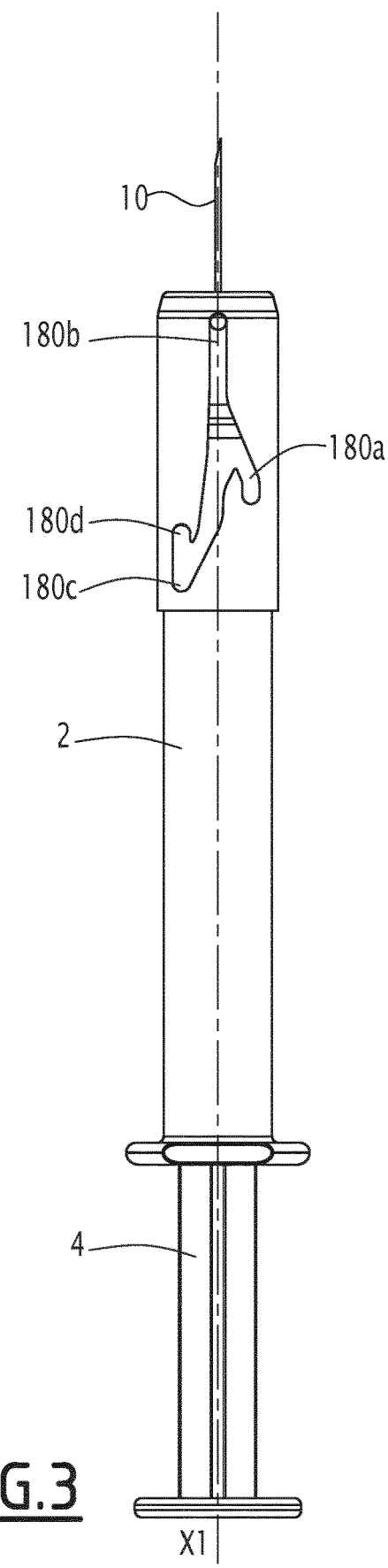
Figure 4:
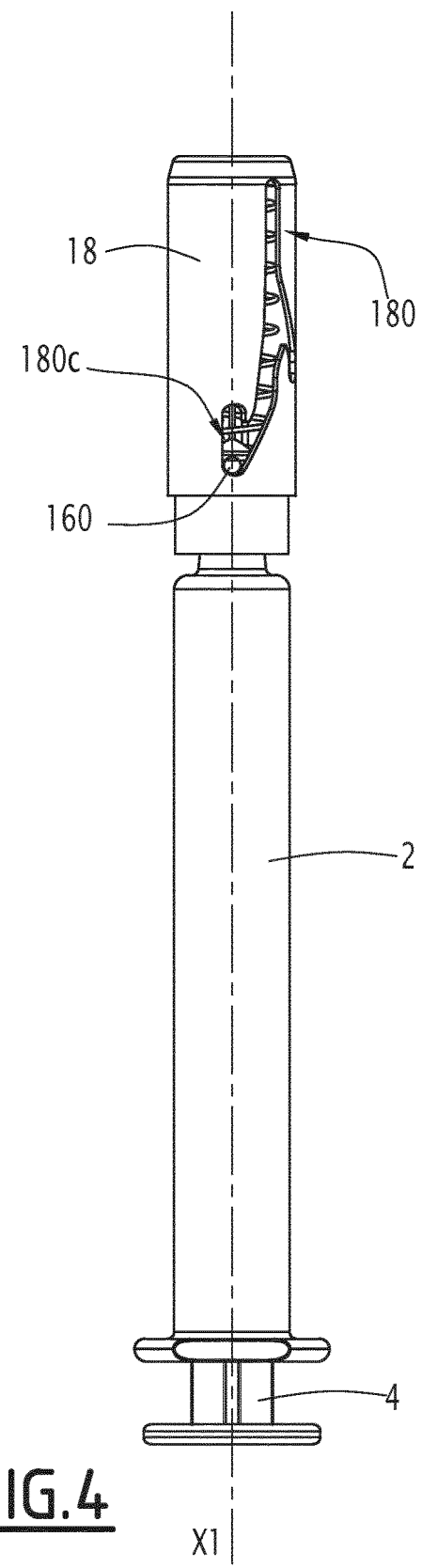
Figure 5:
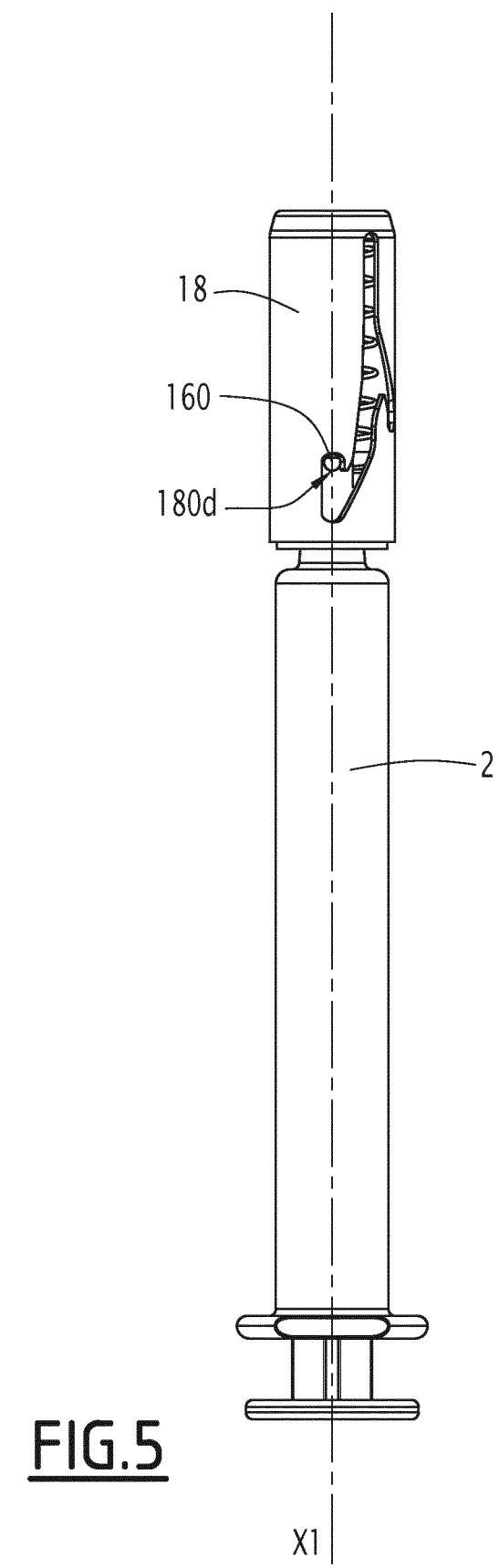

FIGS. 1 and 2 show a syringe 1 with bonded needle. The syringe 1 extends along a longitudinal axis X1 and comprises a syringe body 2 containing an active ingredient P. The syringe body 2 includes a longitudinal end 8 forming the nose of the syringe. The syringe also comprises a hypodermic needle 10 mounted permanently (not removable). The needle 10 is bonded to the inside of a through hole of the end 8 of the body.

The syringe 1 also comprises a piston 6 and a piston rod 4. Advantageously, the piston rod 4 and the piston 6 are screwed one with the other. The piston rod 4 is conventionally used to push the active ingredient P contained inside the syringe body 2 to the inside of the needle 10, which is of course hollow. The piston rod 4 is translatable inside the body 2. It can be maneuvered at a longitudinal end of the syringe, in particular at the end opposite the nose of the syringe.

An after-use safety system 100, shown in FIGS. 6 to 11, is configured to be mounted on a syringe with bonded needle, like that shown in FIGS. 1 to 5, for example. This system 100 serves primarily to cover the needle of the after-use syringe, that is to say, at the end of the injection, in order to avoid accidental sticks with the used syringe. This system in particular serves to protect the personnel handling the after-use syringes.

This after-use safety system 100 comprises a barrel 110, which defines a central axis X100 along which it is translatable and which comprises at least one, preferably two radial openings 112 respectively forming two guide paths for pins 122.

Conventionally, each guide path 112 is globally in the shape of an asymmetrical Y, with the branches of the Y extending toward the rear. The branches of the Y are referenced 112a and 112c, while its central portion is referenced 112b. This central portion 112b is a straight portion, i.e., a corridor.

Figure 7:
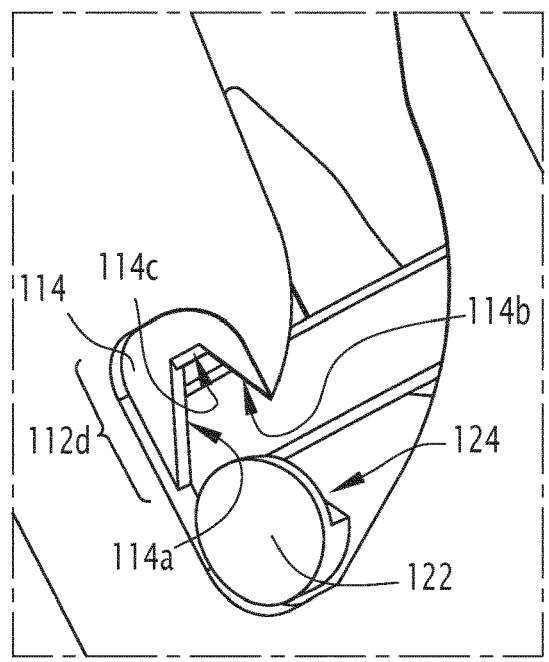
FIG. 7 is an enlarged view of box VII of FIG. 6.
Figure 8:
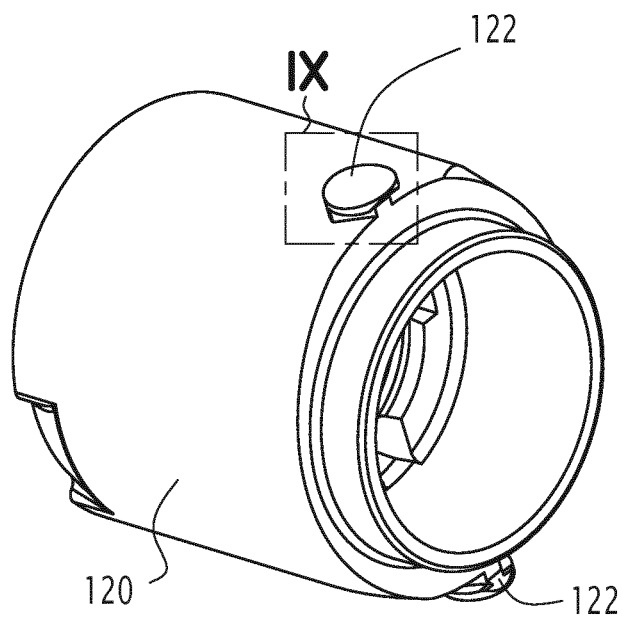
FIG. 8 is a perspective view of the immobilizer belonging to the safety system according to the invention.
Figure 9:
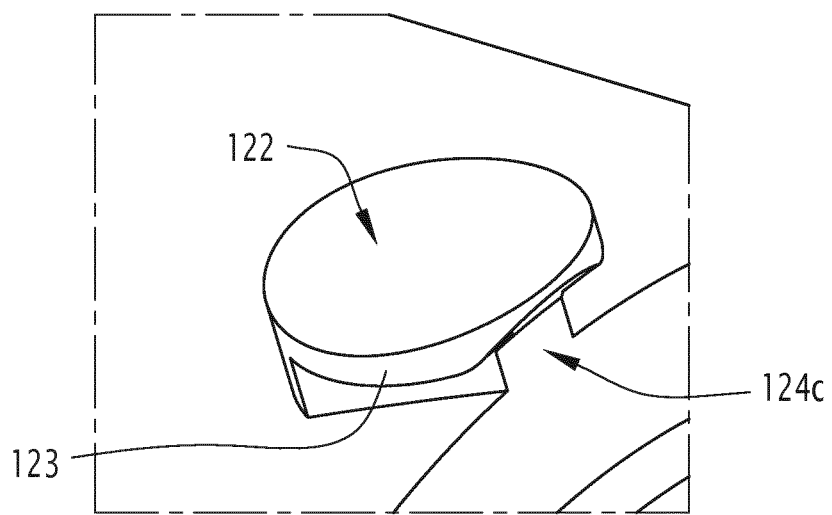
FIG. 9 is an enlarged view of box IX of FIG. 8.

Each guide path 112 cleverly comprises, at one end, in particular at the free end of the branch 112c, a bent portion forming a housing 112d, particularly visible in FIG. 7, inside which a pin 122 is received when the barrel 110 is forced toward the rear after use of the syringe. This housing 112d in fact forms a means for locking the barrel in the covering position of the needle (forward position).

The system 100 also comprises what is called a blocker 120, which is arranged inside the barrel 110 and which comprises the pins 122 cooperating with the barrel 110. The system 100 lastly comprises a return spring 130, in particular visible in FIG. 10 and configured to elastically load the barrel 110 forwards relative to the immobilizer 120.

Figure 6:
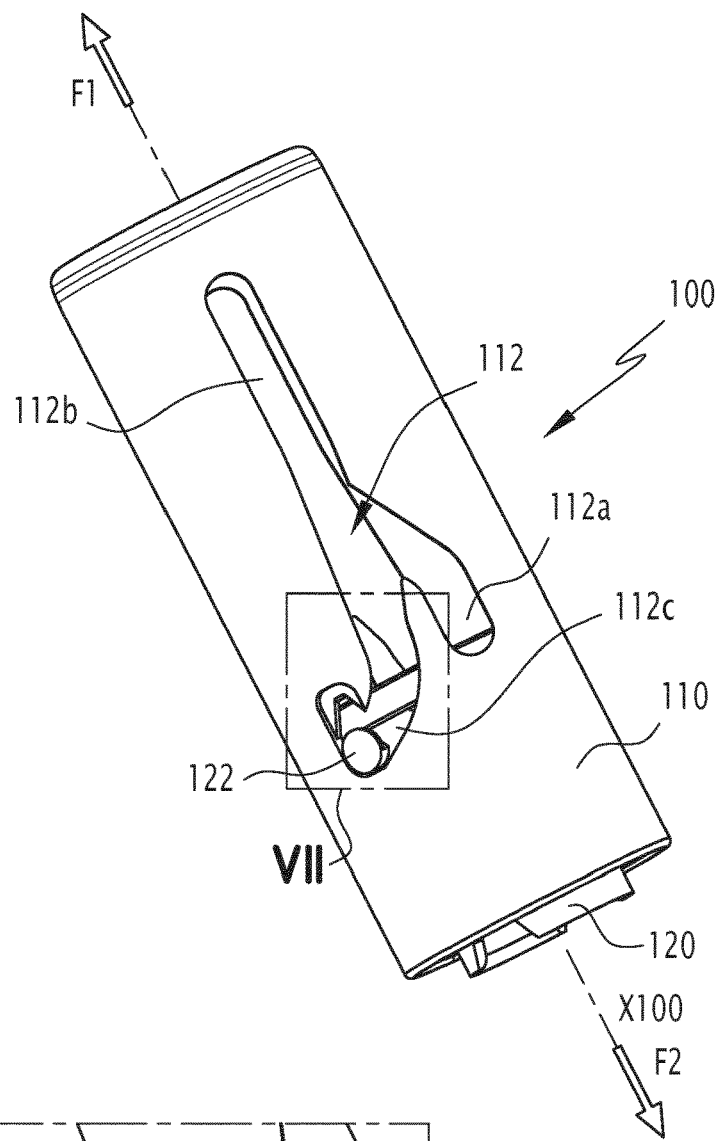
FIG. 6 is a side view of the after-use safety system according to the invention, which comprises a barrel and an immobilizer arranged inside the barrel.

The forward direction is shown in FIG. 6 by an arrow F1, the arrow F2 showing the rear direction. The forward and rear directions are opposite directions parallel to the central axis X100 of the barrel 110.

The barrel 110 is a tubular geometric part centered on the axis X100. The barrel 110 is preferably made from plastic, in particular using an injection molding method.

The immobilizer 120 assumes the form of a globally cylindrical hollow part, also centered on the axis X100. One can therefore say that the immobilizer 120 is arranged coaxially inside the barrel 110. In the example, there are two pins 122 that extend radially outward, here diametrically opposite one another. More specifically, the pins 122 protrude radially with respect to the rest of the body of the immobilizer 120.

Of course, the number of pins 122 is not limiting. In a variant, there could be one, three or even more pins 122. However, there is a guide path for each pin.

Advantageously, each pin 122 does not protrude radially relative to an outer radial surface S110 of the barrel 110. Thus, the maximum diameter of the immobilizer 120 is smaller than the maximum diameter of the barrel 110. This makes the after-use safety system 100 radially compact.

In practice, the immobilizer 120 is configured to be attached, optionally with a possibility of rotation, around the end of the syringe body. For example, the immobilizer 120 may comprise, in a manner known in itself, resilient fastening tabs (not shown).

The spring 130 is a conventional spiral spring, which is arranged inside the barrel 110. The spring 130 comprises a first end in contact with the immobilizer 120 and a second end in contact with an inner radial shoulder of the barrel 110 (see for example FIG. 2). This inner radial shoulder is at one longitudinal end of the barrel, in particular at the front end.

Figure 12:
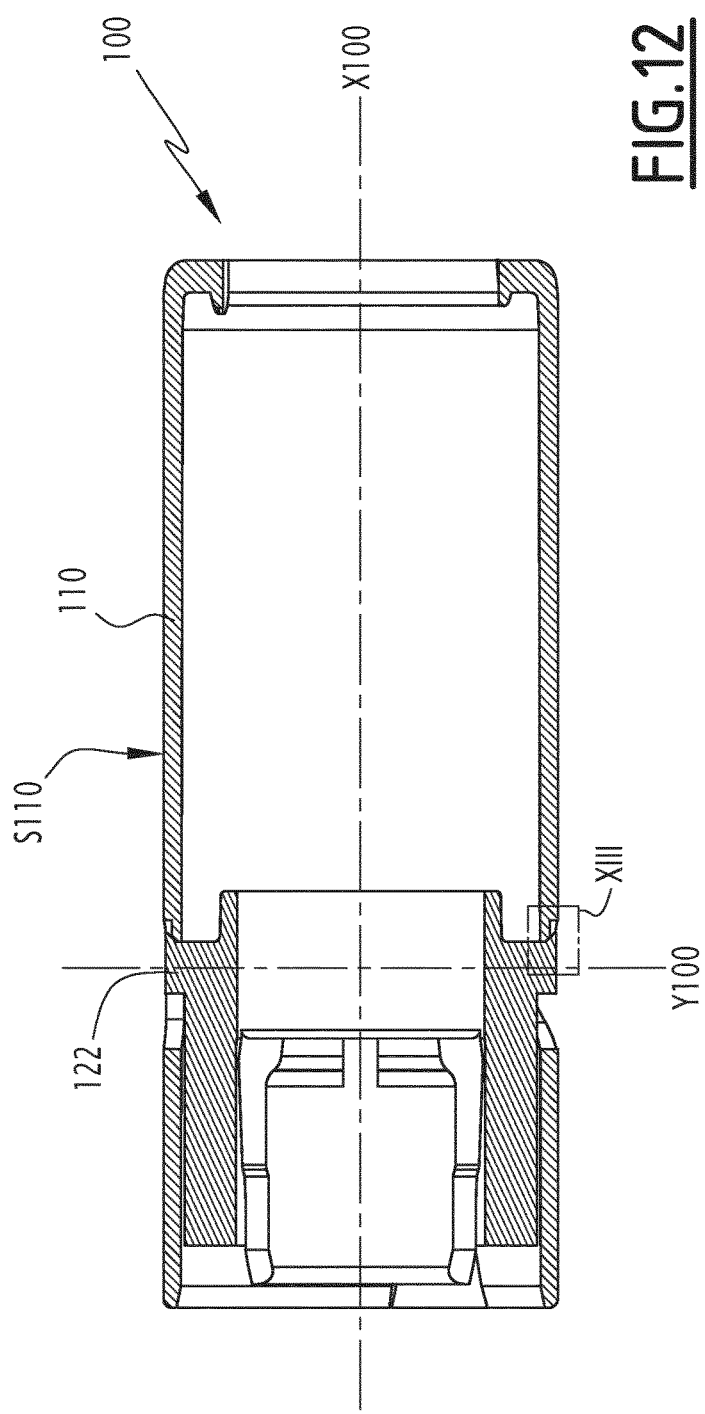
FIG. 12 is a longitudinal cross-section of the after use safety system.
Figure 13:
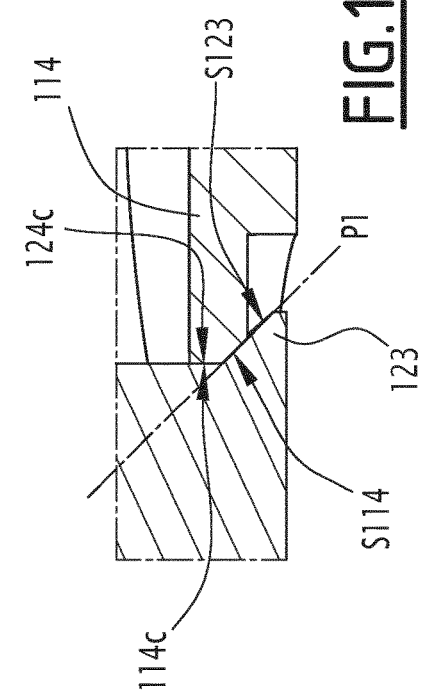
FIG. 13 is an enlarged view of box XIII of FIG. 12.

As shown more particularly in FIGS. 12 and 13, the immobilizer 120 comprises a radial stopping means 123 for immobilizing the barrel 110 along one axis Y100 radial to the central axis X100 when the barrel 110 is forced towards the rear after use of the syringe.

Preferably, the radial stopping means 123 is part of the pin(s) 122. In the example, each pin 122 comprises a radial stopping means 123.

Advantageously, each radial stopping means 123 is a radial end part of the pin, which is arranged opposite the base of the pin, which in turn is secured to the rest of the immobilizer 120.

In the embodiment of the figures, each pin 122 comprises a recess 124 that is partially radially covered by the radial stop means 123. In other words, the radial stop means 123 hides the recess 124 when one looks at the pin 122 from above. This means that the radial stop means 123 is arranged above the recess 124. The recess 124 is dimensioned to receive a portion 114 of the barrel when the barrel 110 is forced toward the rear after use of the syringe.

Here, the portion 114 is formed inside the housing 112*d* formed at the free end of the branch 112*c* of the opening 112.

As shown in FIG. 7, this portion 114 of the barrel 110 advantageously comprises two oblique faces 114*a* and 114*b* that converge one toward the other, preferably symmetrically, in the forward direction.

In the example, the portion 114 of the barrel also comprises a junction face 114*c* between the two oblique faces 114*a* and 114*b*. Preferably, this junction face 114*c* is planar, but it is also possible, in a variant, to imagine that it is convex, that is to say, domed.

In the example, the recess 124 extends over only a portion of the circumference of the pin 122. The recess 124 is arranged at the base of the pin 122.

Advantageously, the walls of the recess 124 comprise two oblique faces 124*a* and 124*b* that converge one toward the other, preferably symmetrically, in the forward direction.

The two oblique faces 124*a* and 124*b* are complementary to those of the wall 114, the oblique faces 114*a* and 114*b* of the portion 114 cooperating with the oblique faces 124*a* and 124*b* of the pin 122 when the barrel 110 is forced toward the rear after the use of the syringe.

The walls of the recess comprise a junction face 124*c* between the two oblique faces 124*a* and 124*b*. Preferably, this junction face 124*c* is planar, but it is also possible, in a variant, to imagine that it is concave, that is to say, hollow.

Advantageously, and as shown in FIG. 13, each radial stopping means 123 includes a stopping surface S123 designed to abut against a surface S114 of the barrel 110 when the barrel 110 is forced toward the rear after use of the syringe. More specifically, this surface S114 is delimited by the part 114 of the barrel previously defined.

In the example, the surfaces S114 and S123, which cooperate in a complementary manner with one another, are inclined surfaces relative to the central axis X100 of the system 100. Thus, and as shown in FIG. 13, the contact plane P1 between the two surfaces S114 and S123 is an oblique plane (that is to say, inclined) relative to a longitudinal or transverse plane of the system 100.

In a variant that is not shown, the surfaces S114 and S123 could be radial surfaces, that is to say, surfaces perpendicular to the radial axis Y100 of the system. More generally, the surfaces S114 and S123 are not each perpendicular to the central axis X100.

Advantageously, the normal of the surface S114 is oriented toward the outside of the system 100, while the normal of the surface S123 is oriented toward the inside of the system. In this way, when the barrel 100 is forced toward the rear after use of the syringe, the pins 122 oppose, owing to the portion 123, the radial expansion of the barrel (out-of-roundness).

Below a certain axial force threshold, typically on the order of 40N, each pin 122 is blocked abutting against the portion 114 of the barrel 110 when the barrel is forced toward the rear after use of the syringe 1.

Conversely, above this threshold, the radial stopping means 123 is torn away in contact with the barrel 11. Thus, one can say that the radial stopping means is, in one preferred embodiment, a removable part of the pin 122 (visible only in FIG. 9), which is removed in contact with the portion 114 of the barrel when the barrel 110 is forced toward the rear after use of the syringe.

In the example, each pin 122 is dimensioned such that the radial stopping means 123 is removed in contact with the barrel 110 once the axial force applied on the barrel exceeds 40N.

Thus, the resistance of the system to a forcible unlocking attempt after use of the syringe henceforth depends on the holding power of the pin(s) of the immobilizer, and not on the resistance of the barrel itself to deformation. In the example where the immobilizer comprises two pins, one can see that the pins are removed from 40N of axial force, versus 20N previously. This is due to the fact that the mechanical resistance of the system to unlocking is no longer based on the mechanical resistance of the barrel to deformation, and in particular to radial expansion (which is relatively low), but rather on the holding power of the pins, which is higher.

After use of the syringe, the system 100 is in the configuration of FIG. 6. From this configuration, if one tries to withdraw the barrel 110, that is to say, if one pushes the barrel 110 in the direction of the arrow F2, then the pin(s) 122 each assume the direction of the housing 112*d*. The faces 124*a* to 124*c* respectively abut against the faces 114*a* to 114*c*. Additionally, the radial stopping means 123 of each pin 122 blocks the radial deformation of the barrel 110, in a localized manner at each pin 122. In the example, since there are two pins 122 and they are arranged diametrically opposite relative to the central axis X100, the radial stopping means 123 of the two pins exert resistance forces that are substantially aligned along the radial axis Y100 and oriented toward one another.

When the radial force exceeds about 40N, the portion 123 of each pin 122 is removed, and each pin 122, then devoid of the portion 123, passes inside the barrel 110. In particular, a certain out-of-roundness of the barrel is observed, that is to say, a localized radial expansion, causing the pin(s) 122 to enter inside the barrel 110, that is to say, to leave the corresponding opening 112.

It will therefore be understood that the pins 122 have a certain breakability, that is to say, a shape that lends itself to breaking, such that when the barrel 110 is forced toward the rear after use of the syringe, the breaking of the pin is observed rather than the deformation of the barrel 110.

The features of the embodiment of the figures and variants not shown may be combined with one another to create new embodiments of the invention.

The invention claimed is:

1. An after-use safety system for a syringe, comprising:
    a barrel defining a central axis along which the barrel moves in translation, the barrel comprising a radial opening forming a guidance path for a pin;
    an immobilizer arranged inside said barrel, the immobilizer comprising:
        a radial stopper for immobilizing said barrel along one axis radial to the central axis when said barrel is forced towards a rear direction of the immobilizer after use of the syringe; and
        said pin interacting with said barrel, said pin comprising a recess at least partially covered by said radial stopper, the recess being dimensioned to receive a portion of said barrel when said barrel is forced toward the rear direction of the immobilizer after use of the syringe, and walls of the recess comprising two oblique faces that converge one toward the other in a forward direction of the immobilizer, the forward direction of the immobilizer being opposite the rear direction of the immobilizer; and a return spring, configured to elastically load said barrel forwards with respect to said immobilizer, in the forward direction of said immobilizer.

2. The after-use safety system according to claim 1, wherein said radial stopper is part of said pin.

3. The after-use safety system according to claim 2, wherein said radial stopper is a radial end part of said pin, which is arranged opposite a base of said pin.

4. The after-use safety system according to claim 1, wherein the portion of said barrel comprises two oblique faces complementary to said oblique faces of the walls of said recess, the oblique faces of the portion of said barrel cooperating with the oblique faces of the walls of said recess when said barrel is forced toward the rear direction of the immobilizer after use of the syringe.

5. The after-use safety system according to claim 1, wherein said radial stopper comprises a stopping surface interacting with a complementary surface of said barrel when said barrel is forced toward the rear direction of said immobilizer after use of the syringe.

6. The after-use safety system according to claim 5, wherein said stopping surface is non-perpendicular to the central axis.

7. The after-use safety system according to claim 5 wherein said stopping surface comprises a normal oriented toward an inside of the system.

8. A syringe equipped with an after-use safety system according to claim 1.

9. The after-use safety system according to claim 1, wherein said oblique faces converge one toward the other symmetrically.

10. The after-use safety system according to claim 5, wherein said stopping surface is inclined relative to the central axis.

* * * * *